(12) United States Patent
Hosseini et al.

(10) Patent No.: US 12,030,046 B2
(45) Date of Patent: Jul. 9, 2024

(54) APPARATUS AND METHOD FOR RAPID IDENTIFICATION OF MICROORGANISMS

(71) Applicant: CITROGENE INC., San Jose, CA (US)

(72) Inventors: S Abbas Hosseini, Los Altos, CA (US); Amir Tork, San Jose, CA (US)

(73) Assignee: CITROGENE INC., San Jose, CA (US)

( * ) Notice: Subject to any disclaimer, the term of this patent is extended or adjusted under 35 U.S.C. 154(b) by 407 days.

(21) Appl. No.: 16/880,754

(22) Filed: May 21, 2020

(65) Prior Publication Data

US 2020/0368744 A1    Nov. 26, 2020

Related U.S. Application Data (60) Provisional application No. 62/851,384, filed on May 22, 2019.

(51) Int. Cl.
*C12Q 1/6888* (2018.01)
*B01L 3/00* (2006.01)
(Continued)

(52) U.S. Cl.
CPC ... *B01L 3/502715* (2013.01); *B01L 3/502738* (2013.01); *C12N 1/06* (2013.01); *C12Q 1/44* (2013.01); *C12Q 1/6888* (2013.01); *C12Q 1/6897* (2013.01); *G01N 21/6428* (2013.01); *B01L 2200/16* (2013.01); *B01L 2300/047* (2013.01); *B01L 2300/06* (2013.01);
(Continued)

(58) Field of Classification Search
CPC ..... B01L 2300/0803; B01L 2400/0409; B01L 2300/1861; B01L 2200/16; B01L 2300/047; B01L 2300/06; B01L 2300/0627; B01L 2300/0883; B01L 2300/168; B01L 2400/06; B01L 2400/0666; B01L 3/502738; B01L 3/50273; B01L 3/502715; C12N 1/06; C12Q 1/6888; G01N 21/6428
See application file for complete search history.

(56) References Cited

U.S. PATENT DOCUMENTS 6,958,132 B2   10/2005   Chiou
7,200,088 B2    4/2007   Worthington et al.
(Continued)

OTHER PUBLICATIONS

Cho et al., "One-step pathogen specific DNA extraction from whole blood on a centrifugal microfluidic device," Lab Chip, vol. 7, pp. 565-573. (Year: 2007).*

(Continued)

*Primary Examiner* — Young J Kim
(74) *Attorney, Agent, or Firm* — Frijouf, Rust & Pyle, P.A.

(57) ABSTRACT

An apparatus and method is disclosed for rapid identification of a microorganism within sampling device. The sampling device has a plurality of reaction chambers each having a different reactive agent for reacting with the microorganism to indicate the presence of a microorganism in said reaction chamber. A detector detects each of the plurality of reaction chamber for detecting the presence of a microorganism in said reaction chamber. The invention automates CRISPR CAS 12 and/or CAS 13 method. The invention is a general platform for detection of segments of DNA or RNA using CRISPR CAS 12 and/or CAS 13 proteins.

6 Claims, 10 Drawing Sheets

(51) Int. Cl.
  *C12N 1/06* (2006.01)
  *C12Q 1/44* (2006.01)
  *C12Q 1/6897* (2018.01)
  *G01N 21/64* (2006.01)

(52) U.S. Cl.
  CPC . *B01L 2300/0627* (2013.01); *B01L 2300/168* (2013.01); *B01L 2300/1861* (2013.01); *B01L 2400/06* (2013.01); *G01N 2021/6439* (2013.01)

(56) References Cited

U.S. PATENT DOCUMENTS

| | | | |
|---|---|---|---|
| 8,222,045 | B2 | 7/2012 | Lee et al. |
| 8,821,814 | B2 | 9/2014 | Cho et al. |
| 9,168,523 | B2 | 10/2015 | Ludowise et al. |
| 9,289,765 | B2 | 3/2016 | Kim et al. |
| 10,252,267 | B2 | 4/2019 | Lee et al. |
| 10,266,887 | B2 | 4/2019 | Abudayyeh et al. |
| 10,451,622 | B2 | 10/2019 | Melanson et al. |
| 2002/0176342 | A1* | 11/2002 | Worthington .... G01N 33/54353 |
| 2004/0191125 | A1* | 9/2004 | Kellogg ........... H01C 17/06586 422/72 |
| 2009/0035847 | A1 | 2/2009 | Cho et al. |
| 2011/0085950 | A1 | 4/2011 | Lee et al. |
| 2011/0256026 | A1* | 10/2011 | Kim ................ G01N 33/54386 422/68.1 |
| 2012/0293796 | A1* | 11/2012 | Ludowise .............. G01N 35/04 356/244 |
| 2019/0310247 | A1 | 10/2019 | Tak et al. |

OTHER PUBLICATIONS

Gaspar et al., "Magnetically controlled valve for flow manipulation in polymer microfluidic devices," Microfluid Nanofluid, vol. 4, pp. 525-531. (Year: 2008).*

Sanchez-Ferrer et al., "Liquid-Crystalline Elastomer Microvalve for Microfluidics," Advanced Materials, vol. 23, pp. 4526-4530. (Year: 2011).*

Jacqueline R. Rettig and Albert Folch, Large.Scale Single.Cell Trapping And Imaging Using Microwell Arrays, Anal. Chem. 2005, 77. 5628-5634.

Jacqueline R. Rettig and Albert Folch, Large.Scale Single.Cell Trapping And Imaging Using Microwell Arrays, Supporting Information for.

Jeong-Gidi Lee, Kwaog Ho Cbeoog, Nam Huh, Suhyeon Kim, Jeong-Woo Choi and Christer Ko, Microchip-based one step DNA extraction and real-time peR in one chamber for rapid path.

886 Lab Chip, 2006, 6, 886-895, The Royal Society of Chemistry 2006 www.rsc,org/loc.

Cho et al., One-step pathogen specific DNA Extraction . . . , Lab Chip, 2007, 7, 565-573, The Royal Society of Chemistry 2007 www.rsc,org/loc.

Gaspar et al., Magnetically Controlled Valve for Flow Manipulation in Polymer microfluidic device, Microfluid Nanofluid 2008 4:525-531.

Sanchez-Ferrer, Liquid-Crystalline Elastomer Microvalve for Microfluidics, Advanced Materials 2011, 23, 4526-4530 www.wileyonlinelibrary.com.

* cited by examiner

APPARATUS AND METHOD FOR RAPID IDENTIFICATION OF MICROORGANISMS

BACKGROUND OF THE INVENTION

Field of the Invention

The present invention is related to the field of medical diagnostics and more particularly to a micro fluidic device designed to manage all the clinical steps to detect range of microorganisms and pathogens in a single sample body.

Description of the Related Art

Demand for highly compact analytical biochemical systems incorporated lab-on-chip micro fluidic devices is beginning to gain momentum. Improvements in accuracy, total analysis, rapid time of analysis, cost effectiveness, low sample volume, performance and user friendliness are the criteria required in each product.

There are big efforts in different biomedical research labs and biomedical companies to develop systems for rapid identification of microorganisms and pathogens (mainly bacteria and fungi or viruses) in the blood or urine of patients. The global healthcare systems is still struggling for an standard diagnostic chip to make early and effective treatment decisions, especially in the incidence of new pathogens. There are several millions blood infections occurring globally each year, the major of the infections happen in third world countries where there is no regular access for medical services. In addition, the extreme hospital costs in developed countries mandate the decrease in patient length of stay in hospitals to decrease hospital costs to improve pattern health.

There are well known diagnostic methods which are based on the phenotypical or molecular characteristics of pathogens. Generally pattern blood sample is sent to clinical diagnostic labs and the sample is processed for bacteria culture. It takes few days if not longer for the bacteria to grow under special conditions. Experts visually diagnose the samples. The morphological features of bacteria give pathologists the indication of type of the infection. However, this method requires a considerable amount of time, consumables, equipment, aseptic environment, and trained personnel.

Fluorescence In-Situ Hybridization (FISH) is another common diagnostic method which is based on fluorescence emission of the complementary probes to the pathogen genetic material. A sample is loaded on a slide, permeabilized, fixed and then hybridized with specifically designed probes. The sample is then washed a few times to remove the unattached pathogens and reagents. The pathogens hybridized with the probes are visualized under fluorescent microscope to analyze the existence of the pathogens. Now the sample is excited by laser light generally at the blue spectrum and the sample will fluoresce at the green spectrum if there are any pathogens. The absence of the green fluorescent light indicates that there has been no hybridization between the bacteria and the probes. The test needs to be repeated again with other probes to evaluate the existence of the suspicious bacteria as it is clear, the process is slow and needs a professional to do the experimental steps.

There are also immunodiagnostic approaches, in which an antigen antibody reaction as a primary means of detection. Two predominant formats of such devices are the Enzyme-Linked Immuno Sorbent Assay (ELISA) and the Lateral-Flow test (LFD), also known as the dipstick. Antibodies specific for a desired antigen can be conjugated with a radiolabel, fluorescent label, or color-forming enzyme which are applied as a probe. Well known applications of these methods include pregnancy tests, distinguishing blood types, and detection of microbes and drugs in vivologies. This method is considered as an effective method, but like most other techniques, it also has some shortcomings such as, the availability of the antibody in the market, the lengthy process of specific antibody production (weeks to months), the need for trained personnel, frequent pipetting and washing steps, and more importantly the specificity of the antibodies.

Nucleic acid based methods are generally specific and highly sensitive for small amount of specimens and can be used for different type of microorganisms (including the nonviable or inactivated ones). These techniques are particularly useful for organisms that are difficult to culture. Polymerize Chain Reaction (PCR) is one of the most widely used molecular biology technique in the category of molecular diagnosis. PCR is very efficient, reliable and fast. However, the high sensitivity of these assays carries high risk of cross-contamination due to the operator involvement, and the number of steps. Another shortcoming of this assay is related to the non-specific annealing of the primers to sequences that are similar, but not completely identical. In addition, since these techniques rely on enzymatic activity, in the presence of any reagent contamination which inhibits the enzyme activity, false-negatives could occur. Requirement for experienced personnel to prepare and operate the assay are some other drawbacks of this assay. Nevertheless, it is still one of most accurate and widely used method in the hospitals for the patients in urgent condition. Generally, in one hour the existence of the specific pathogen scan be assessed.

Bacteriophages are pervasive viruses that infect bacteria, and employ their genetic machinery to replicate themselves. Bacteria have developed an adaptive immune system called Clustered Regularly Interspaced Short Palindromic Repeats (CRISPR). CRISPR is consisted of identical repetitive DNA sequences (28 to 37 base pairs), with un-identical spacer DNA regions (21 to 72 base pairs) in between the repeats that exactly match the genomic sequence of the previously invading viruses, enables bacteria to remember the viruses. If the same viruses (or closely related ones) attack the bacteria again, the bacteria can transcribe RNA sequences from the CRISPR arrays to target the viruses' genetic material. The bacteria then use Cas proteins which have helices and nuclease activity to unwind the DNA and cut the DNA apart, which deactivates the virus. The arrangement of CRISPR base is a unique for different bacteria and can be used as their finger print. Cas12a (for ssDNA and dsDNA) and Cas13 (for ssRNA) are two of the Cas protein family members. When the programmable gRNA binds to a specific RNA or DNA target of a pathogen, the two enzymes become activated and cleave all nearby RNA molecules. By combining this complex with a labeled RNA repeater which has a fluorophore and a quencher on the two ends, the activated C as protein cleaves there porter RNA, creating a measurable fluorescent signal which indicates the existence of the pathogen. However, this method needs a pre-amplification of the extracted pathogen.

Genetic material which would be done through the isothermal recombinase polymerase amplification (RPA) procedure which would be done using basic temperature control equipment. Fabricating proper device to use this revolutionary technique is the subject of the present invention.

Therefore it is an object of the present invention to provide in apparatus and method for rapid identification of microorganisms involving the clustered regularly interspaced short palindromic repeats (CRISPR).

Another object of the present invention to provide an apparatus and method for rapid identification of microorganisms that operates in a batch format and has random access capabilities.

Another object of the present invention to provide an apparatus and method for rapid identification of microorganisms that is affordable and reliable.

Another object of the present invention to provide an apparatus and method for rapid identification of microorganisms that is simple to setup and run enabling in ordinary technician to operate the machine in the field with minor training.

Another object of the present invention to provide an apparatus and method for rapid identification of microorganisms that is equipped with sample processing, testing and reporting.

Another object of the present invention to provide an apparatus and method for rapid identification of microorganisms that has a rapid short turn-around time.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an apparatus and a method for rapid identification of a microorganism within sampling device, the micro fluidic sampling device. The micro fluidic sampling device has a plurality of reaction chambers each having a different reactive agent for reacting with the microorganism. The reaction with the microorganism indicates the presence of a microorganism in the reaction chamber.

The apparatus comprises a grabber for holding the sampling device. A laser is positioned to irradiate the micro fluid sampling device. A motion stage is connected to the grabber for moving the sampling device in a plane for position portions of the micro fluidic sampling device relative to a beam from the laser. A detector defects light emitted from each of the plurality of reaction chambers for detecting the presence of a microorganism in the reach on chamber.

In a more specific embodiment of the invention, the micro fluidic sampling device comprises a main reservoir for receiving the sample and isolating the microorganism containing portion of the sample. A collection reservoir receives the microorganism containing portion of the sample from the sample reservoir. A plurality of reaction chambers each having a different reactive agent. The microorganism containing portion is transferred by a capillary microchannel to each of the plurality of reaction chambers for reacting with the microorganism to indicate the presence of a microorganism in the reaction chamber.

In another more specific embodiment of the invention, the micro fluidic sampling device is a rotatable disk having a central hole. The grabber engages with the central hole for holding the rotatable disk. A motion stage comprises a slider for radially moving the rotatable disk and a motor for rotating the rotatable disk. The laser can irradiate selective portion of the micro fluidic sampling device upon movement of the motion stage. The laser may be used for irradiating the micro fluidic sampling device to heat a sample in the micro fluidic sampling device to effect lysing of the sample. In addition, the laser may be used to irradiate the micro fluidic sampling within in each of the plurality of reaction chambers to indicate the presence of a microorganism in reaction chamber. Preferably, a spectrometer detector detects light emitted from each of the plurality of reaction chambers for detecting the presence of a microorganism in the reaction chamber.

In another more specific example of the micro fluidic sampling device, the device composes a sample body having a main reservoir for receiving the sample and isolating the microorganism containing portion of the sample. A collection reservoir receives the microorganism containing portion of the sample from the sample reservoir. A plurality of reaction chambers each has a different reactive agent. A capillary micro channel transform the microorganism containing portion to each of the plurality of reaction chambers for reacting with the microorganism to indicate the presence of a microorganism in the reaction chamber. Preferably, the sample body is transparent and fabricated from glass. The glass enables the laser to heat process the sample.

A main reservoir value is interposed between the main reservoir and the collector reservoir from controlling the flow into the collector reservoir and a collector reservoir valve is interposed between the collector reservoir and the capillary macro channel for controlling the flow into the plurality of reaction chambers. The main reservoir valve and the collector reservoir valve may be a magnetically operated valve or an optically operated valve.

The invention is also incorporated into a method for rapid identification of a microorganism in a sample comprising the steps of introducing a sample into a sample reservoir. A poison of the sample containing the microorganism is isolated from the sample. The microorganisms containing portion of the sample are collected into a collection reservoir. A different reactive agent is introduced into each of a plurality of reaction chambers. The microorganism containing portion is transferred into each of the plurality of reaction chambers. Each of the plurality of reaction chambers is sequentially illuminated for detecting the presence of a microorganism in that reaction chamber.

In a more specific example, the sample containing the microorganism is isolated from the sample by heating the sample by a laser. The apparatus and method of the present invention is suitable for use with the CRISPR Technique as described hereinafter.

The present invention offers different platforms, to serve the diagnostic application on different bodily fluids such as blood, urine, saliva, semen, and etc. Here, infected liquid for, the designed platform for the identification of example the pathogens in the blood explained. In one example, whole blood is injected into the disk, and then the plasma containing bacteria is separated from the disk starts rotating. At high speed rotation heavy elements such as red and white blood cells through a rapid sedimentation process in the rotating disk separated from plasma and bacteria. Therefore, the disk acts similar to micro-centrifuge. Then the plasma and bacteria follow through a hole to the next section while being irradiated by a focused laser beam. At the focus bacteria wall is lysed and DNA is released. This method is very efficient to open up fungi wall as well. Then the sample is guided to the 36 reaction chambers. Each chamber has three key ingredients of (1) protein CAS 12 and/or CAS 13; (2) random labeled RNA molecules with a fluorophore and a quencher on the two ends; (3) one individual type of gRNA molecules which is complementary to the generic material of the pathogens under question. The gRNA molecules could be programmed to target only the pathogens which their whole genome is already sequenced and is available in the database.

Different enzymes are used to create CRISPR RNA in short crRNA. Then the sample is guided to 36 reaction chambers. In the reaction chambers 36 different complement of crRNA for top infectious diseases are placed that is called guide RNA in short gRNA also protein CAS 12 and/or CAS 13 are present. The third element in the chambers is the random RNA. The random RNA is common for all the chambers and has two fluorescent indicator molecules attached to a generic designed RNA from each side. All three ingredients of gRNA, CAS 12/13 protein said random RNA reporter RNA are freeze dried and can be stored inside the disk for a king period of time (years). The disk is vacuum sealed and packaged in a black dark cover to avoid any interactions with light. If there is unknown bacteria a pathogen for which a complementary gRNA molecule exist in the reaction chambers, were in the list of the gRNA in that specific reaction chamber the hybridization takes place between and the genetic material of the pathogen, crRNA and the gRNA and consequently the CAS 12/13 protein gets activated. This specific protein starts to cut cleave any nearby RNA including the reporter RNA. The fluorescently labeled reporter emits measurable fluorescence when cleaved by the RNase activity of CRISPR-Cas system. This results in major changes in the radiated fluorescent when the reaction chamber excited with the pump laser. In traditional diagnostics methods each bacteria or segment of the DNA or RNA of the bacteria can generate only one signal. To amplify the signal we need to amplify the bacteria by cultivating culturing them or increase the segment of the DNA or RNA of the bacteria by PCR to increase the signal level. CRISPR CAS 12/13 uses interesting idea, instead of amplifying the signal by amplifying the source it uses the presence of the source as a switch to turn on and the signal generation is done by the CAS 12/13 and the reporter RNA. These two elements molecules are beside each other all the time in the reaction chamber but reaction starts when the crRNA genomic target is hybridized with gRNA.

The present invention is based on the development of a new glass based micro fluidic device and method in which all the biosensors and proteins and enzymes are located in the one specific reservoirs. Some of the advantages of the present invention are:

The plasma liquid will fill the reservoirs by relative vacuum power and spinning process, this is a simple but efficient technique to avoid using internal or external pump to move the liquid.

In situ centrifuging to separate different species of the liquid such as extraction of plasma liquid and bacteria from red and white blood sample.

In situ cell lysing to rapture the cell wall and release the DNA and RNA.

Another major advantage is to use minimum amount of sample to do many tests at the same time.

The CRISPR based diagnostics is ample and very accurate;

Read out is fast and it helps to get the accurate results very fast;

Device is portable and light and consumes very low amount of energy.

Low cost due to multiplex analyses in each run;

Disk has CD size structure and am be stored from −50?C to +50?C without need for refrigerator or specific location to store, and therefore it can be stored in the room temperature without needing any refrigeration;

Disk is recyclable and has less harm to the environment;

Cost effective;

User friendly;

Can be used at point of cares and borders (e.g. airports).

The foregoing has outlined rather broadly the more pertinent and important features of the present invention in order that the detailed description feat follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1A:
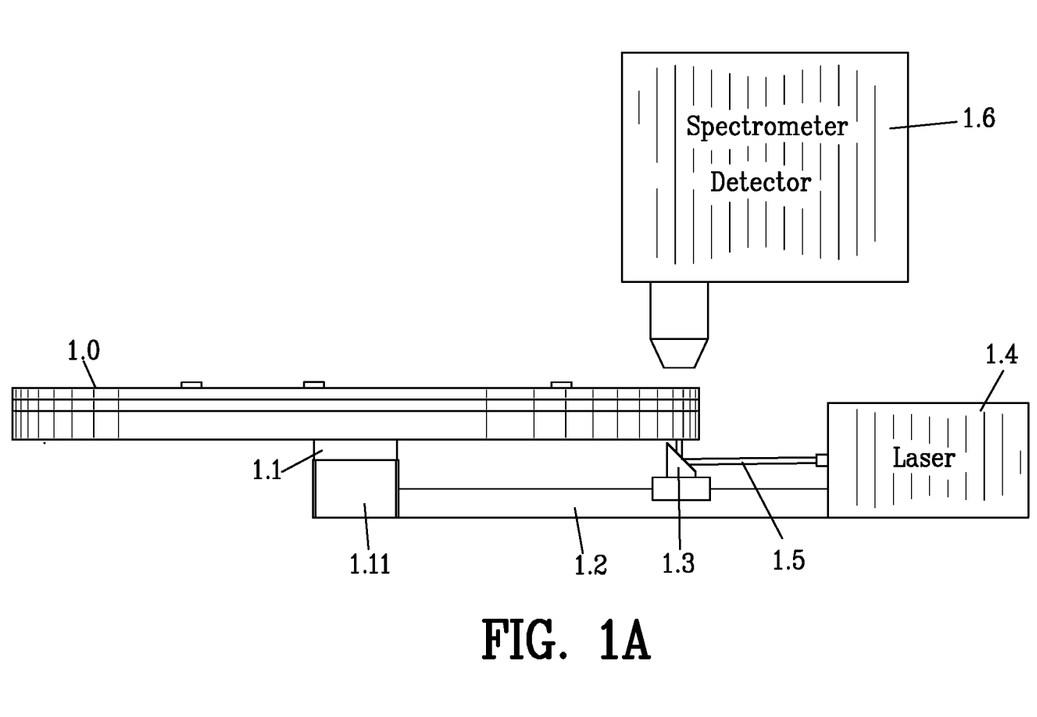
FIG. 1A is a side view of an apparatus for rapid identification of microorganisms of the present invention.
Figure 1B:
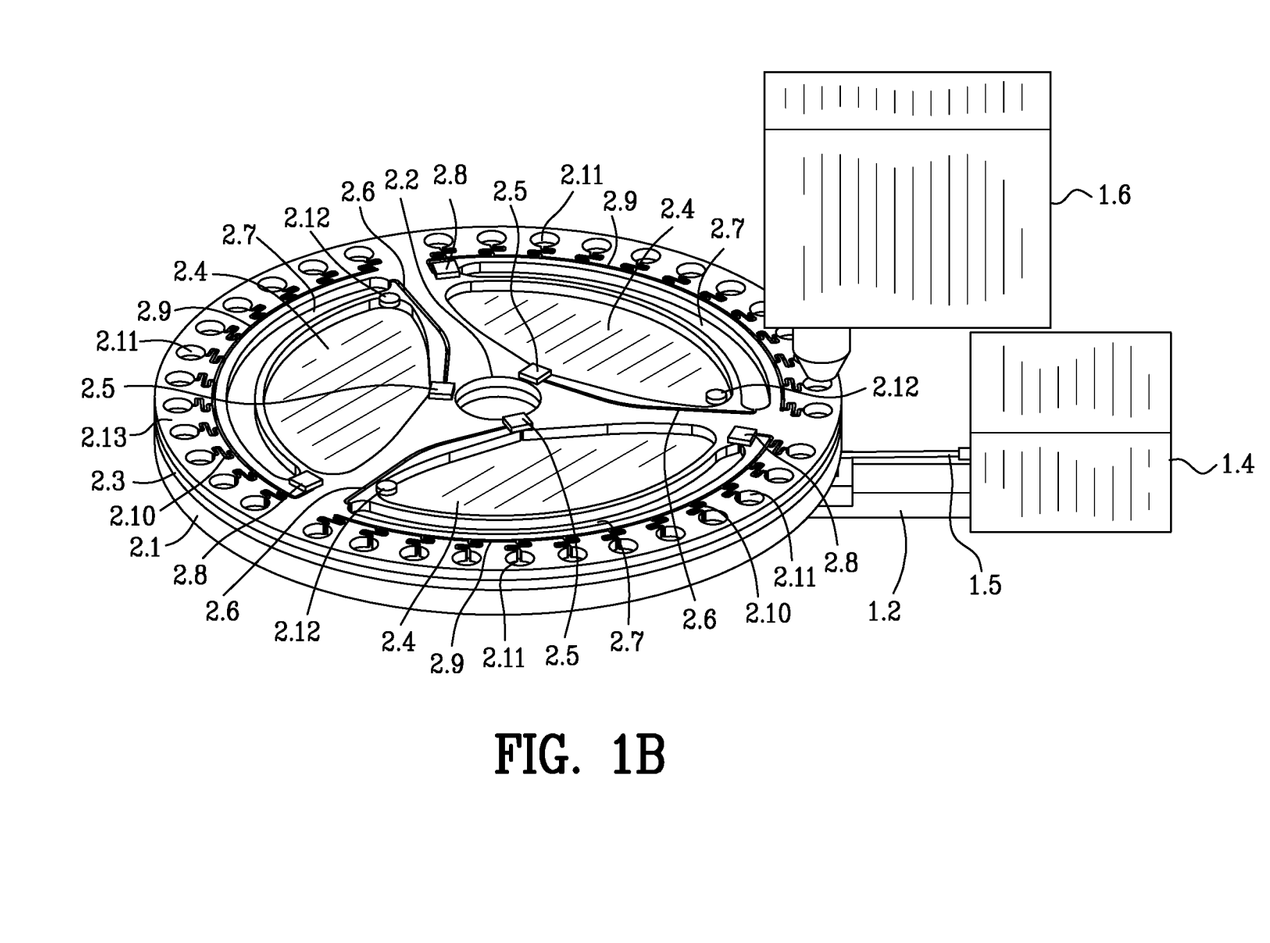
FIG. 1B is an isometric view of the device of FIG. 1A: further illustrating a rotary disk.

FIGS. 1a and 1b illustrate an apparatus for rapid identification of a microorganism such as a bacteria, fungi and viruses. The apparatus is suitable for use with a CRISPR CAS 12/13 diagnostics method. The apparatus receives a micro fluidic sampling device 1.0 for rapid identification of a microorganism within the fluid sample device 1.0. As will be described in greater detail hereinafter, the micro fluid sampling device 1.0 receives a sample for analysis. The micro fluidic sampling device 1.0 is interchangeable and disposable for rapid identification of a microorganism. The micro fluidic sampling device 1.0 is able to diagnose a sample such as blood sample for the well known bacterial infections. However, the micro fluidic sampling device 1.0 can be designed for virus or fungi detection as well.

In this example, the micro fluidic sampling device 1.0 is shown as a rotary disk 1.0 having an approximate size of a compact disk (CD). The apparatus comprises a grabber 1.1 for holding the rotary disk 1.0. The grabber 1.1 includes a motor 1.11 mounted on a motion stage 1.2 for rotating the rotary disk 1.0.

An optical manor 1.3 reflects a laser beam 1.5 from a laser source 1.4 to the rotary disk 1.0. The optical mirror 1.3 can move on the rail 1.2. The rotation of the rotary disk 1.0 and the motion of the optical mirror 1.3 on the rail 1.2 allow the laser beam 1.5 to access essentially any part of the rotary disk 1.0. A spectrometer detector 1.7 measures the passing through and/or emitted from selective parts of the rotary disk 1.0.

FIGS. 2A-2D are enlarged views of a micro fluidic sampling device 1.0 incorporated into a rotary disk 2.0. The rotary disk 2.0 comprises a base layer 2.1 formed from transparent material such as glass or any other material with preferred thickness of 500-700 µm as a structural base of the rotatable disk 2.0. The base layer 2.1 stabilizes the remaining thinner layers of the rotary disk 2.0. A hole 2.2 is defined in rotary disk 1.0 for enabling the grabber 1.1 to hold and to rotate the rotary disk 1.0.

Figure 2A:
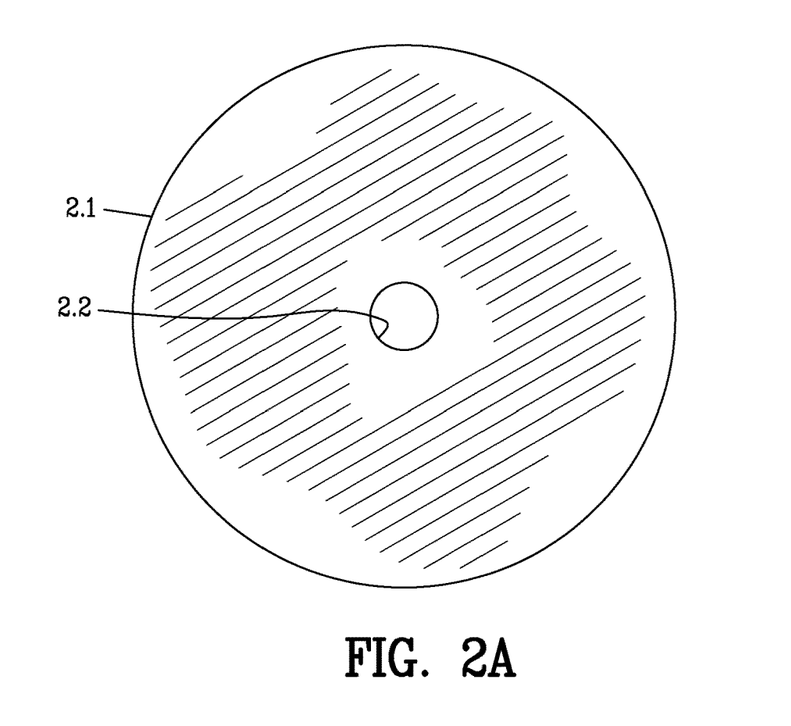
FIG. 2A illustrates a base layer of the rotary disk.
Figure 2B:
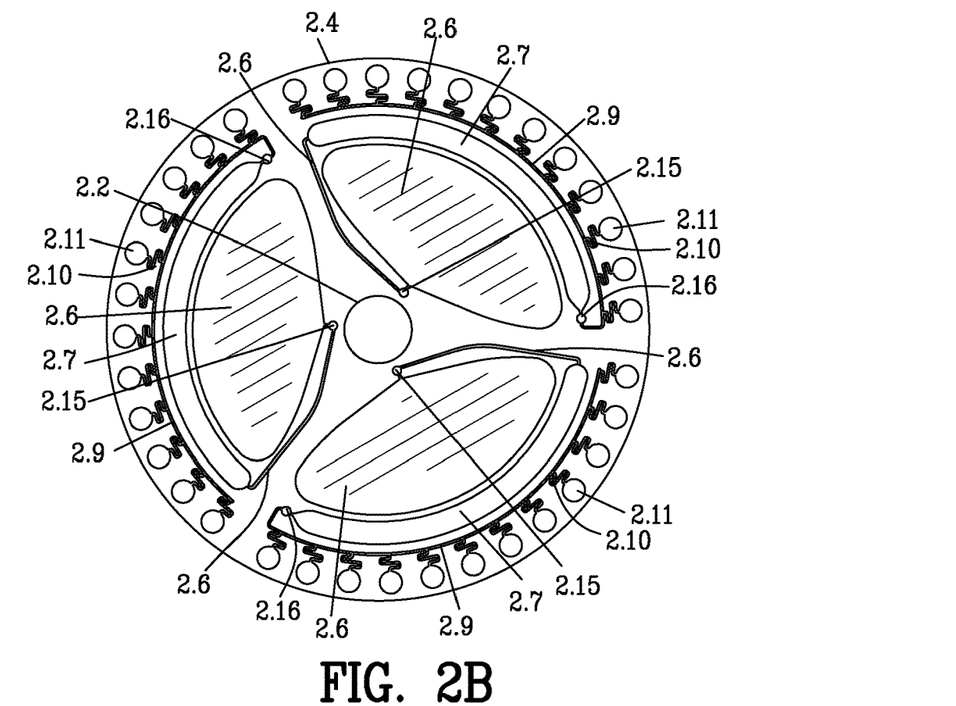
FIG. 2B illustrates a main layer of the rotary disk wherein a reactions will take place.

FIG. 2b is the main layer 2.3 of the rotary disk 2.0 has a concentric central hole forming a part of the hole 2.2 of the rotary disk. The main layer 2.3 is formed from transparent material such as glass or my other material. A main reservoir 2.4 is defined in the main layer 2.3 for receiving the sample to be tested. A main reservoir valve 2.5 connects the main reservoir 2.4 to a capillary channel 2.6. The capillary channel 2.6 communicates with a collector reservoir 2.7 enabling the main reservoir valve 2.5 to control the flow into the collector reservoir. A collector reservoir valve 2.8 controls the flow of fluid from the collector reservoir 2.7 through a capillary micro channel 2.9 to a plurality of reaction chambers 2.11.

A plurality of resistance channels 2.10 are interposed between the capillary micro channels 2.9 and the plurality of reaction chambers 2.11 to inhibit backflow from the plurality of reaction chambers 2.11 into the capillary micro channel 2.9.

Figure 2C:
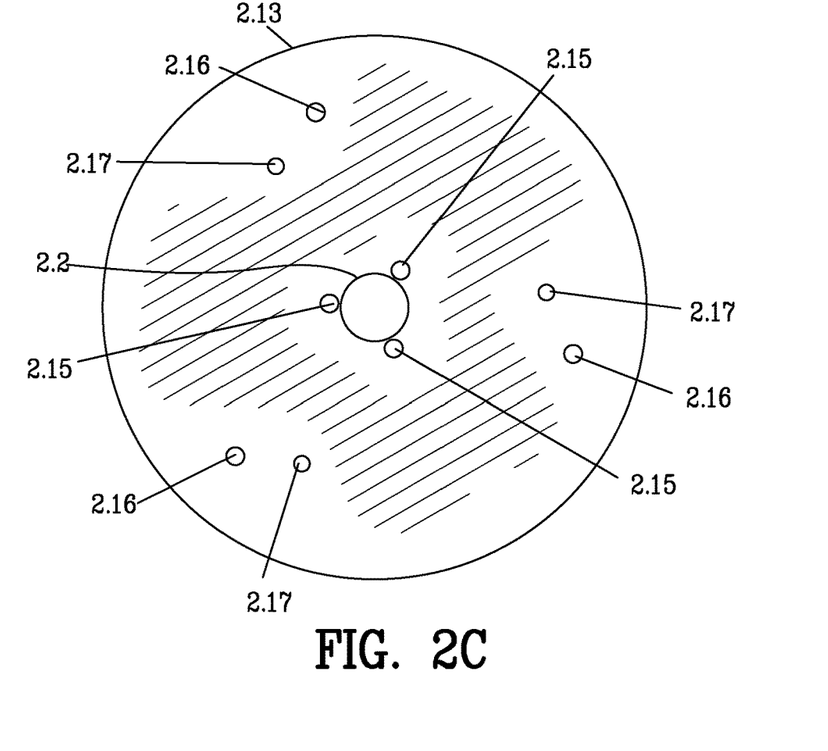
FIG. 2C illustrates a cover layer of the rotary disk.

A cover layer 2.13 overlies the main layer 2.3. Base layer 2.1 and the main layer 2.3 as well as the cover layer 2.13 are secured in a vacuum tight arrangement about the circumference of the rotary disk 2.0 as well as the circumference of the central bole 2.2.

Figure 2D:
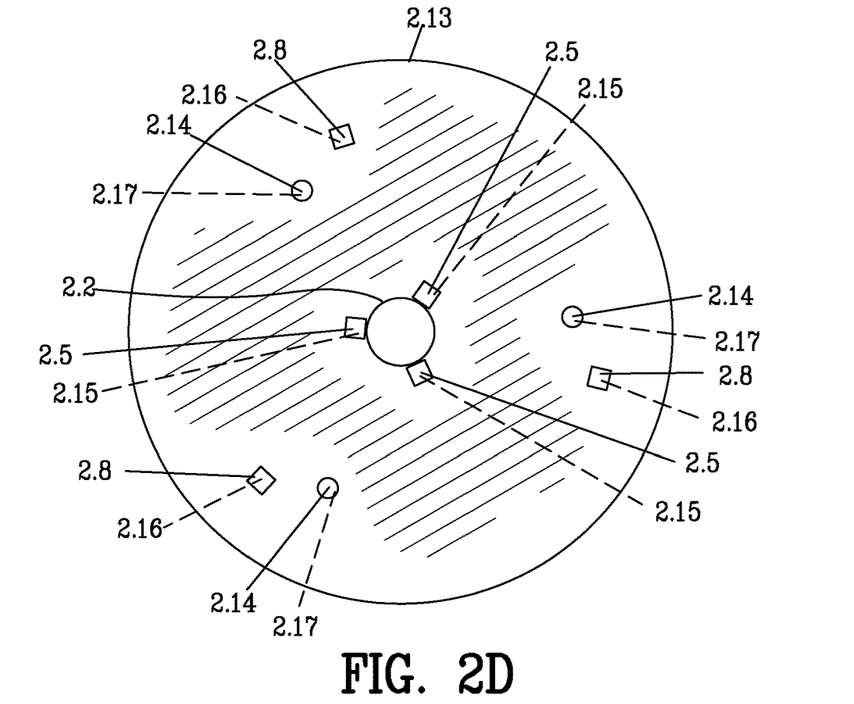
FIG. 2D illustrates the cover layer of the rotary disk equipped with resin injection covers and valves.

The cover layer 2.13 includes an inlet 2.14 for introducing a sample liquid into the rotary disk 2.0. In addition, the cover layer 2.13 includes an aperture 2.15 for receiving the main reservoir valve 2.5 as well as an aperture 2.16 for receiving the collector reservoir valve 2.8. A sealing plug 2.17 is provided for sealing the inlet 2.14 after the introduction of a sample into the rotary disk 2.0. An explanation of the main reservoir valve 2.5 as well as the collector reservoir valve 2.8 will be described in greater detail hereinafter.

In some circumstances that there are many patients and doctors are looking for few common diseases not all of the 36 types of pathogens, then rotary disk 2.0 can be programmed for 12 different pathogens and each run can take three different samples. The rotatable disk 1.0 may be marked aid bar coded (not shown) so each reaction chamber has a unique identification. The device is flexible and can be filled with biomaterials based on customer needs.

Method of Operation

In das example, the rotary disk 2.0 contains thirty-six reaction chambers 2.11 enabling 36 different tests to be simultaneously ran from a single rotary disk 2.0. In the matter of 30 minutes sample will be examined for 36 different types of the photogenes. However, it should be understood by those skilled in the art that the rotary disk 2.0 may be modified in design to accommodate more or less tests chambers. In some circumstances that many sample tests needs to be run each disk can run three different samples at the same time for 12 diagnostics types.

An example of the method of operation of the apparatus is set forth below. The sample, such as a blood sample is introduced into one of the three sample injection locations 2.14 and the sealing insert plug 2.17 is installed to close the three sample injection locations 2.14.

The rotary disk 2.0 is then placed into the apparatus. When the rotary disk 2.0 starts to rotate, due to centrifugal force blood plasma and bacteria separated from the heavy species such as red and weight blood cells. Red blood cells move outwards wink blood plasma moves towards the center of the rotary disk 2.0. Bacteria also move more towards the center of the rotary disk 2.0. At this point the laser source 1.4 starts irradiating towards the center of the rotary disk 2.0 and increases sample temperature of the blood sample to near 150° C. The last fabrication of the rotary disk 20 enables the blood samples to be heated to the above temperature. At this localized heat lysing start to take place. Cell walk start to rapture and the DNA and RNA are released. The centrifugal force and/or the heat isolates desired microorganism containing portion of the sample from the remainder of the sample.

Upon opening of the main reservoir valve 2.5, the extracted DNA/RNA and plasma liquid will move out to the capillary channel 2.6 to enter the collector reservoir 2.7. In collector reservoir 2.7, different types of enzymes are stored in the form of freeze dried. The enzyme selection is based on the type of the photogenes that will be diagnosed in the reaction chambers 2.11. The enzymes function is to pick the proper DNA and do the cutting at the desired pair locations. If the desired photogene exist in the sample now has the segments of DNA or RNA ready for detection. To have redundancy and increase the signal to noise level it is preferred to pick at least three different segments of the DNA or RNA for detection.

By activating this collector reservoir valve 2.8, the DNA/RNA segments that are floating in the plasma liquid will transfer into the capillary micro channel 2.9. The capillary micro channel 29 distributes the sample among twelve reaction chambers 2.11. The resistance channel 2.10 is designed in the path to avoid leakage of the freeze dried powders from reaction chambers 2.11 towards the capillary channel 2.9. When the DNA/RNA segments arrived in the reaction chambers 2.11, DNA/RNA segments react with the freeze dried powders stored within the reaction chambers 2.11. The reaction between the DNA/RNA segments react with the freeze dried powders wifi be explained in greater details with reference to FIG. 7.

The laser beam 1.5 propagates through a reaction chamber 1.6 within the rotary disk 1.0. The laser beam 1.5 irradiates from the laser source 1.4 to the optical mirror 1.3 to be focused on the rotary disk 2.0 to excite florescence molecules within the reaction chamber 1.6. A spectrometer detector 1.7 measures the excite florescence molecules within the reaction chamber 2.11. If any reaction takes place then that specific reaction chamber 2.11 will emit green fluorescence signal when excited by the blue diode laser.

Advantages of Glass

Preferably, the rotatable disk 2.0 is fabricated from glass since glass has the many advantages over thermal plastic based cartridges. Glass has a number of unique properties that are beneficial for a number of differed applications in Life Sciences, Biomedical. These unique properties include:
- Excellent optical transparency, with a low fluorescence background;
- Great mechanical strength, thermally stable and scratch resistant;
- Chemically inert, impermeable for liquids and gases making it biocompatible.

These unique properties make glass highly desirable for many applications however, the traditional fabrication methods available today such as mechanical cutting/dicing/drilling, laser ablation, water jet cutting, and photolithography wet/dry etching are not capable of creating the complex high aspect ratio microstructures that researcher, engineers and designers are looking to achieve for their products.

In the last 3 to 5 years there have been a number of developments in the area of "Selective Laser Assisted Etching" to address the demands for glass devices with high precision features. However, these new developments are very costly, they are time consuming and difficult to scale to address higher volume markets. Because of these issues, the industry has had to resort to using PMMA and/or Thermal Plastics to address their needs. FDMS and thermal plastics while on the surface those appear to be a more cost-effective solution, they still have a number of drawbacks that make them a less desirable. Both require a mold for each of the different devices being produced, these molds have a finite lifespan and need to be replaced, became the utilize molds it is difficult to make product design changes, because the molds have to be designed and can be expensive to redesign. Both PDMS and thermal plastics can have issues with fluorescence, and they are also incompatible with many organic solvents. For cell lysing high temperature operation is desired which is the melting point of the most plastics.

The present invention provides a fast, cost effective and scalable glass micro fabrication processes that can address the needs of the ever-expanding Life Sciences. The present laser-based solution is fast, economic, highly controlled and sealable for volume production. The present process is designed to work with nearly all the common glass material currently being used today in life sciences. The present process does not rely on expensive molds to fabricate the devices and are able to make changes to the device features with a few key strokes, also our process does not require the need for costly nano-fabrication devices such as the ones used in photolithography methods.

Figure 3A:
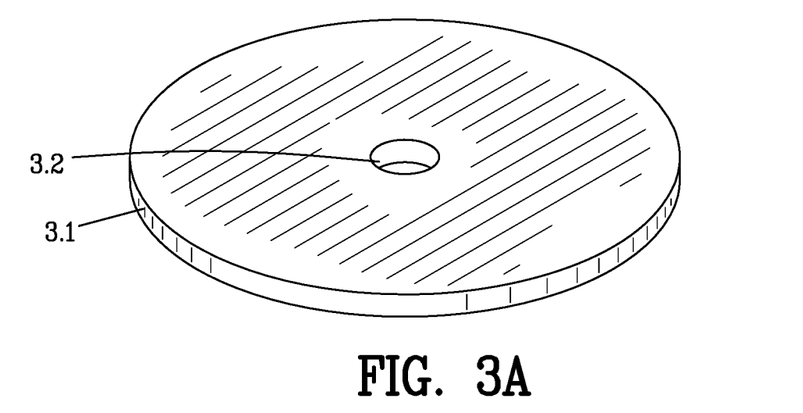
FIG. 3A illustrates a base layer of a second embodiment of the rotary disk for the apparatus of FIGS. 1A and 1B.
Figure 3B:
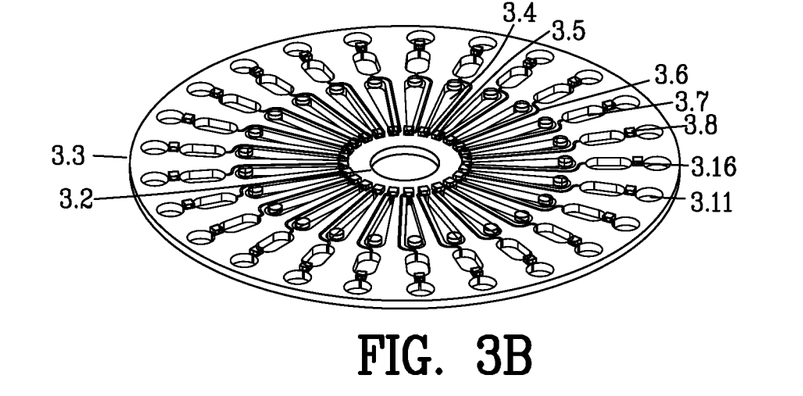
FIG. 3B illustrates a main layer of the second embodiment of the rotary disk of FIG. 3A.
Figure 3C:
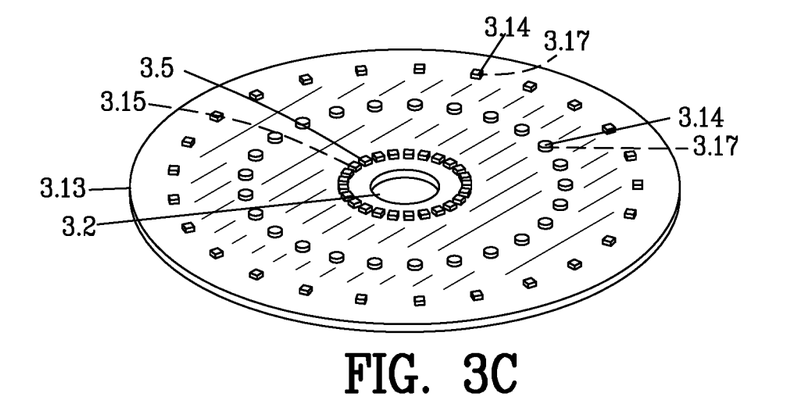
FIG. 3C illustrates a cover layer of the second embodiment of the rotary disk equipped with resin injection covers and valves.

FIGS. 3A-3C illustrates a second embodiment of the present inversion. In this embodiment the rotary disk 3.0 is redesigned to take many samples at the same time and do the detection for a single microorganism or pathogen. The rotary disk 3.0 is designed to respond to a region of the world experiencing a disease pandemic similar to Ebola or Zika virus or an army is being faced with bio thread similar to Anthrax. Instead of diagnosing each sample for 36 types of the pathogens, the rotary disk 3.0 examines as many people as possible in the single run for one specific infection. In current design twenty-five reaction chambers, equally spaced barriers are independently placed in the rotary disk 3.0. Another clear use of this invention is in agriculture. Suppose a gardener would like to examine all of the fruit trees for a specific disease. Then collected samples from each tree bar coded and loaded in a single disk.

The rotary disk 3.0 comprises a base layer 3.1 formed from transparent material such as glass or any other material with preferred thickness of 500-700 µm as a structural base of the rotatable disk 3.0. The rotary disk 3.0 defines a hole 3.2 enabling the grabber 1.1 to hold and rotate the rotary disk 3.0.

FIG. 3B illustrates a main layer 3.3 of the rotary disk 3.0 formed from transparent material such as glass or any other material. A main reservoir 3.4 is defined in the main layer 3.3 for receiving the sample to be tested. A main reservoir valve 3.5 connects the main reservoir 3.4 to a capillary channel 3.6. The capillary channel 3.6 communicates with a collector reservoir 3.7 enabling the main reservoir valve 3.5 to control the flow into the collector reservoir 3.7. A collector reservoir valve 3.8 controls the flow of fluid from each of the collector reservoirs 3.7 to a respective reaction chamber 3.11. An explanation of the main reservoir valve 3.5 as well as the collector reservoir valve 3.8 will be described in greater detail hereinafter.

FIG. 3C illustrates a cover layer 3.13 of the rotary disk 3.0 formed from transparent material such as glass or any other material. Base layer 3.1 and the main layer 3.3 as well as the cover layer 3.13 are secured in a vacuum tight arrangement about the circumference of the rotary disk 3.0 as well as the circumference of the central hole 3.2.

The cover layer 3.13 includes inlets 3.14 for introducing a sample liquid into the rotary disk 3.0. In addition, the cover layer 3.13 includes apertures 3.15 for receiving the main reservoir valve 2.5 as well as aa aperture 2.16 for receiving the collector reservoir valve 2.8. A sealing insert plug 3.17 is provided for sealing the inlet 3.14 after the introduction of a sample into foe rotary disk 3.0.

Method of Operation

A sample such as a blood sample is injected into the inlet 3.14 of the main reservoir 3.5 and the insert plug 3.17 is inserted to seal the inlet 3.14. The rotation of the rotary disk 3.0 separates the plasma liquid and pathogens from red and white blood cells due to centrifugal force. The plasms liquid and pathogens move towards outside the center of the rotary disk 3.0. By applying the laser beam 1.5 towards the center of the rotary disk 3.0, the lysing process struts md the wall of the pathogens cracks down to release the DNA and RNAs.

When reservoir valve 3.5 is activated, the liquid that contains the DNA and RNAs will pass through capillary channel 3.6. The curved capillary channel 3.6 transfers the sample from the main reservoir 3.5 to the collector reservoir 3.7. Specific, frizzed dried enzymes are placed inside the collector reservoir 3.7. The enzymes are activated when mixed with liquid. The enzymes cut the DNA and pick specific segment of the DNA or RNAs. The picked specific segments of the DNA or RNAs are referred to as crRNA.

When the collector reservoir valve 3.8 is activated, the crRNAs move to the reaction chamber 39. Inside the reaction chamber the CAS 12/13 protein with gRNA and random RNA is placed. All of these biomaterials are freeze dried to last for years if stored from light and humidity. If the crRNA hybridize with gRNA, then CAS 12/13 protein is activated resulting in cutting of any RNA including the random RNA's.

The integration of proper micro-valve into micro fluidic devices is a challenging subject since valves needs to function without leakage and error. Also it needs to be robust, simple, low cost and easy to integrate into the micro fluidic device. The micro-valves can be categorized into five different groups.

Mechanical Active Micro-Valve

Using surface micromachining technologies, where mechanically movable membranes are coupled to magnetic, electric, piezoelectric or thermal actuation methods. Most mechanical active micro-valves couple a flexible membrane to magnetic, electrostatic, piezoelectric or thermal traditionally. To miniaturize micro-valve, electrostatic actuation is one of the best candidates. But, it is difficult to obtain high forces and large differences due to extremely high voltages requirement. Concerning the piezoelectric actuation, it is possible to achieve a very high forces but for very small deviations high voltages needed. Thermal actuation can provide a great deal forces via big shots but is relatively slow and cannot be suitable for many fluids due to heat dissipation. So, the magnetic baaed micro-valve could be an excellent choice from this category and will be discussed separately in this work.

Non-Mechanical Active Micro-Valve

The examples include actuation principles based on electrochemical, phase change in rheological materials. Phase change actuation mechanisms such as liquid crystal elastomer, hydrogel, sol-gel, paraffin. In addition, electro-rheological materials or ferro fluids can be used for the non-mechanical active micro-valves. These phase change micro-valves are relatively new and cheap compared to the traditional mechanical active micro-valves. These non-mechanical active micro-valves are of particular interest in terms of their simple device structure and disposability, making them well suited for applications in life sciences.

The micro-valve based on intelligent material, in general is an oriented nematic side-chain liquid crystal elastomer that has the viscoelasticity properties and very weak intermolecular interaction that will be discussed here.

External Active Micro-Valve

In general this type of macro-valve works by using an external system as built-in modular or pneumatic means. In general, external active micro valve operates using an external system as in integrated modular or pneumatic means. The use of external systems is one of the most practical approaches to designing micro-valves. This actuation, is advantageous in the absence of leakage flux at high inlet pressures, but miniaturization may be difficult due to the need for additional external systems.

Mechanical Passive Micro-Valve

Most passive micro-valves, or check valves, are incorporated in inlets and outlets of reciprocal displacement micro-pumps, as mechanical moving parts. Most common passive micro-valve are flaps, membranes, spherical balls or mobile structure. Another type of mechanical passive micro-valve for PCR chip application is based on gel photopolymerization method. In this method a local gel plugs will be created by in situ photopolymerization in the micro channel. This local gel plugs functions as passive micro-valve effectively preventing bulk flow of liquid due to the thermally induced pressure differences during thermal cycling. This method is very slow and is not suitable for fast DNA analysis.

Non-Mechanical Passive Micro-Valve

By using some sort of nozzle, diffuser or Tesla elements in inlets and outlets of reciprocal displacement micropumps. In PCR microfluidic device the passive non-mechanical is based on surface properties; hydrophobic or hydrophilic and is used for controlling the fluid flow in the microchannel. Certain chips could be equipped with access ports that were connected to the main channel for definite positioning of fluid plugs. By coating these ports with hydrophobic Teflon substances the structures could be used as passive stop valves without any external sensor. This type of micro-valve is not reliable because the coated hydrophobic film can be affected by the surfactants which are often included in the PCR mixture.

Although many types of valves may be incorporated within the present intention, two types of micro-valves are shown incorporated with the present intention. A first preferred valve is a non-mechanical active valve such as an intelligent liquid crystal elastomer. A second preferred valve is mechanical active micro-valve such as magnetic based micro-valves. Both micro-valves can be embedded in the micro fluidic device.

Figure 4A:
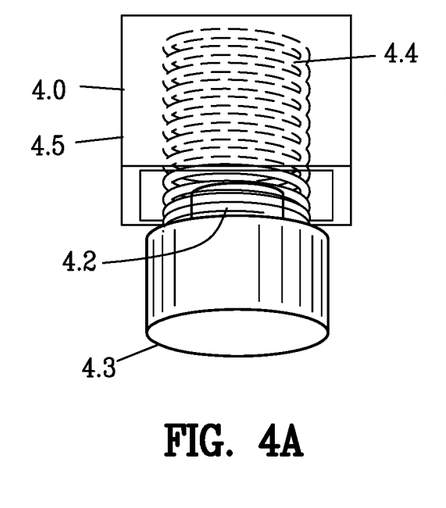
FIG. 4A is an isometric view of a magneto-mechanical valve in a closed position.
Figure 4B:
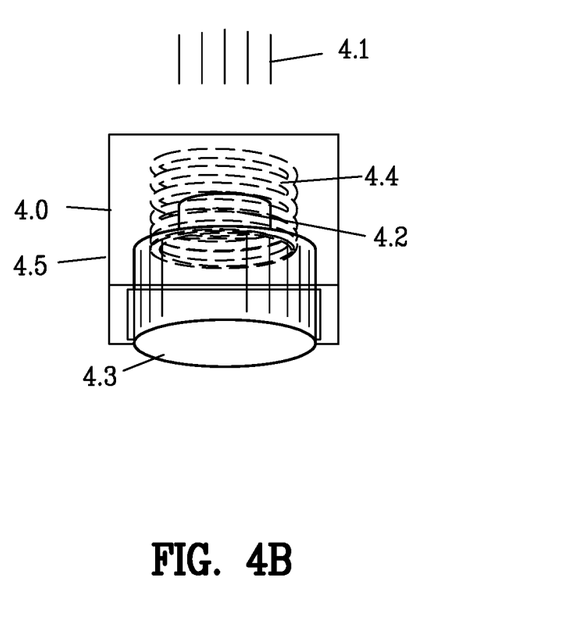
FIG. 4B an isometric view of a magneto-mechanical valve in an open position.

FIG. 4A and FIG. 4B are isometric views of a magneto-mechanical valve 4.0 in a closed position and an open position. For magnetic based micro-valve 40 an external magnetic field 4.1 will be used for the activation. The magnetic based micro-valve 40 with zero leakage and excellent characteristic will be embedded into the micro fluidic devices. The magnetic based micro-valve 40 comprises a permanent rod magnet 4.2 covered or attached by an elastomer polymer 4.3. This type of valves has shown excellent characteristics of no detectable leakage flow up, zero dead volume, keeping its surface mountable capability over the macro fluidic devices. The magnetic rod 4.2 is pushed always down by spring 4.4. The spring is attached to the cover layer. Entire valve parts are assembled and connected to each other and if is inserted in the valve position holes as previously shown. The housing box 4.5 is glued to the cover layer. The spring type is compression and it always pushes the magnet and the elastomer down to close the micro channels in the device.

By using this type of micro-valve the power consumption is reduced and has last response time. In the case of magnetic micro-valve an external magnetic field 4.1 will be applied from top of the box 4.5 to actuate and control the micro-valve operation. When the external magnetic field 4.1 is applied it moves the magnetic rod 4.2 towards itself causing opening of the channel and the flow of liquid.

Figure 4C:
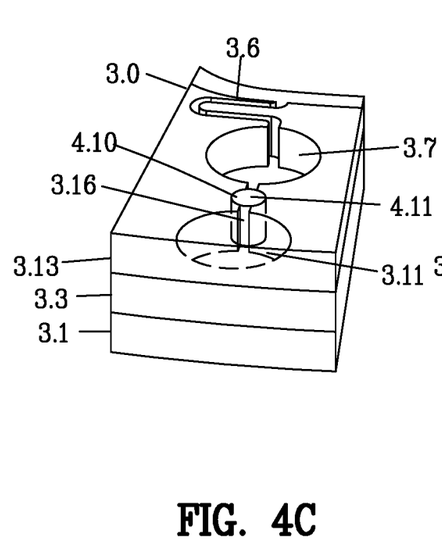
FIG. 4C an isometric view of an isotropic phase of a liquid crystal elastomer in a closed position.
Figure 4D:
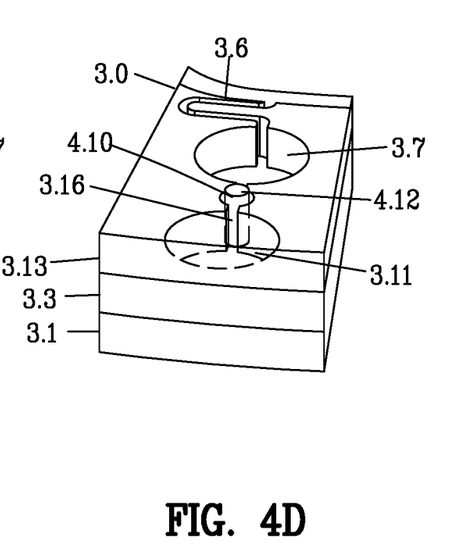
FIG. 4D an isometric view of an isotropic phase of a liquid crystal elastomer in an open position.

FIG. 4C and FIG. 4D are isometric views of an isotropic phase of a liquid crystal elastomer valve 4.10 in a closed position 4.11 and an open position 4.12. For the other type of the micro-valve prepared with the intelligent liquid crystal elastomer, the same laser source that is used for the cell lysing and fluorescence excitation will be used. The main reason to use this kind of liquid crystal elastomer is because reversible and controllable extension is then fundamental property. In this invention we present integration of a liquid crystal elastomeric micro-valve in which the degree of cross-linkages and polymer chain's length will be optimized to reach the maximum reversibility when an external stress applied, such as mechanical stress, temperature change or light exposure. This elasticity property will be optimized to increase the reversibility of foe polymer without any hysteresis to increase the performance of integrated micro-valve in the micro fluidic device.

The direction of extension of the elastomeric micro-valve will be designed parallel to direction of the director of the molecule and parallel to the channel's wall and flow of the fluid, so with applying in external power source, the flow of the liquid can be controlled. Desired characteristics of such micro-valves are zero leakage, without dead volume, detachable from the surface, fast response time, long shelf time, low power consumption and contaminant-free. All parameters given above play an important rote in flow of the liquids in micro fluidic devices.

Figure 5A:
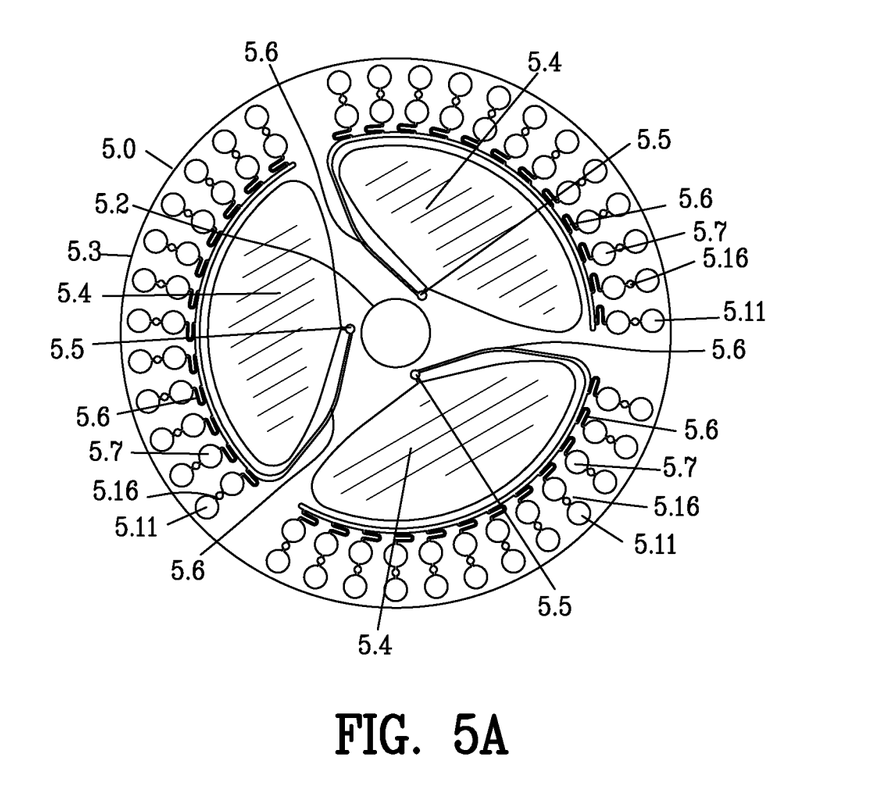
FIG. 5A illustrates a main layer of a third embodiment of the rotary disk.
Figure 5B:
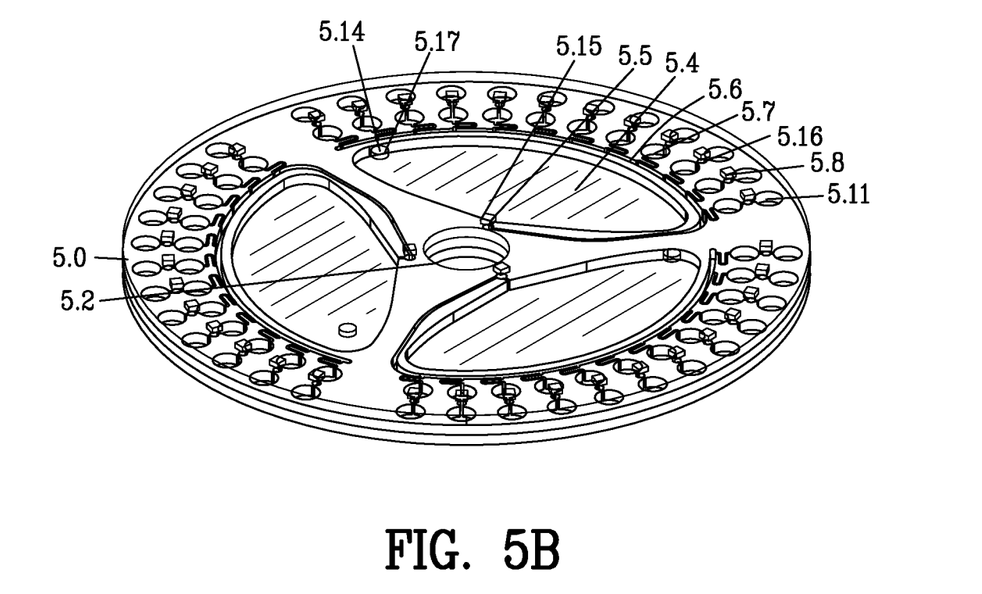
FIG. 5B presents the full assembly rotary disk of FIG. 5A.

FIGS. 5A and 5B illustrate a main layer 5.1 and the cover layer 5.13 of the third embodiment of the invention. The base layer (not shown is similar to FIG. 3A. The main layer 5.1 of the rotary disk 5.0 is modified to have an exclusive collector reservoir 5.11 for each pathogen. The main layer 5.1 of the disk 5.0 defines a central hole 5.2 and a main reservoir 5.3. An aperture 5.15 receives a reservoir valve 5.5 to transfer the liquid from the main reservoir 5.3 to a U-shape micro channel 5.6. The U shape micro channel 5.6 is designed to avoid the biomaterials that are placed in the collector reservoir 5.7 to move into the micro channel 5.6. A collector reservoir valve 5.8 is located in an aperture 5.16. After the extracted generic material of crRNA is produced in the collector reservoir 5.7, the collector reservoir valve 5.8 is activated and the sample moves to the reaction chamber 5.11. The sample is hybridized with the gRNA in the reaction chamber 5.11.

A major difference between rotary disk 5.0 of FIG. 5 and the rotary disk 2.0 of FIG. 2 is the collector reservoir 5.7 is not common for the 12 reaction chambers 5.11. Each reaction chamber 5.11 has its own collector reservoir 5.7. In addition, the reaction chamber 5.11 and the collector reservoir 5.7 may be unified to reduce the number of valves to three in entire rotary disk 5.1. Under this configuration, the collector reservoir 5.7 and the reaction chamber 5.11 become one chamber and the collector reservoir valve 5.8 is removed.

Figure 6A:
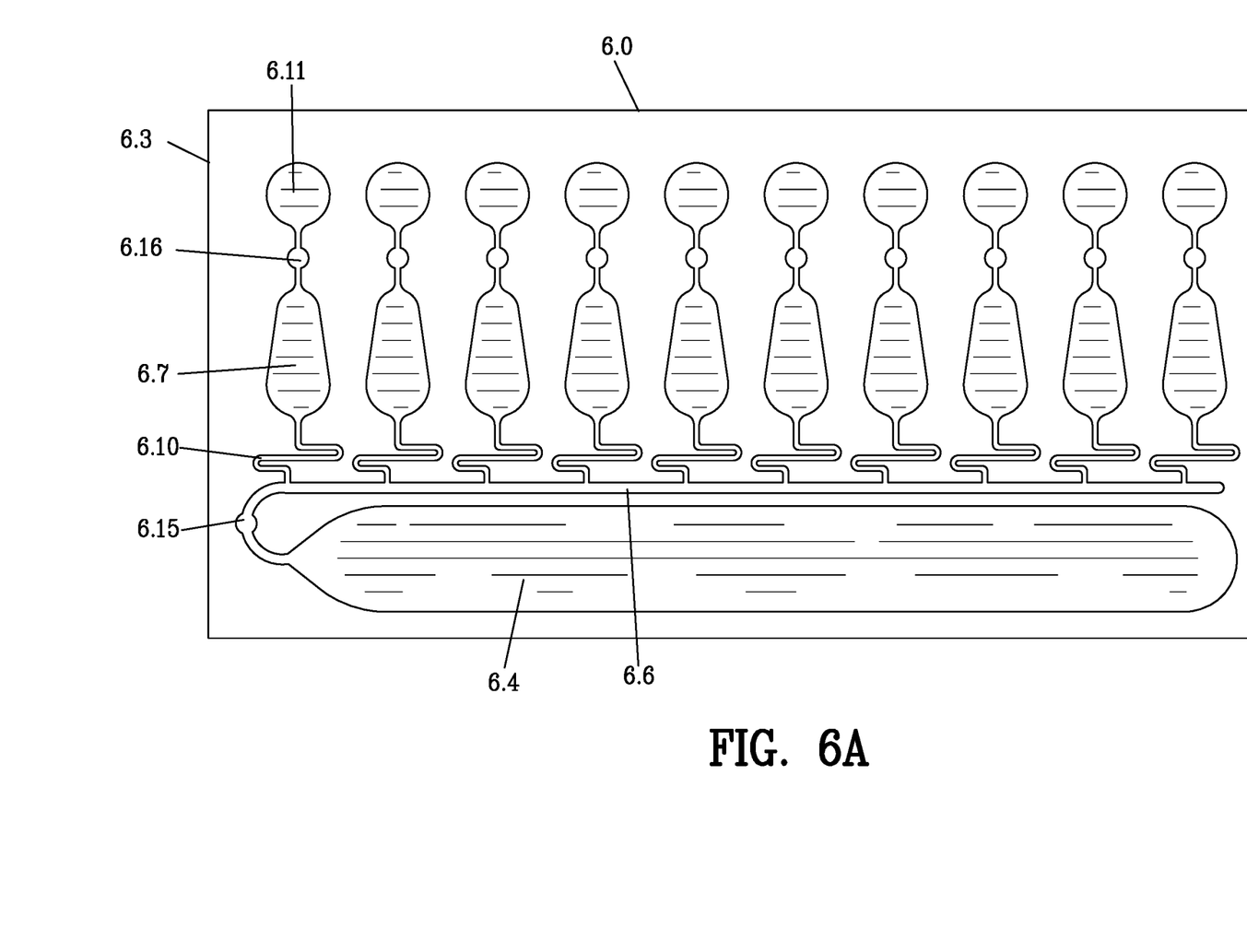
FIG. 6A illustrates a main layer design for a liner cartridge.
Figure 6B:
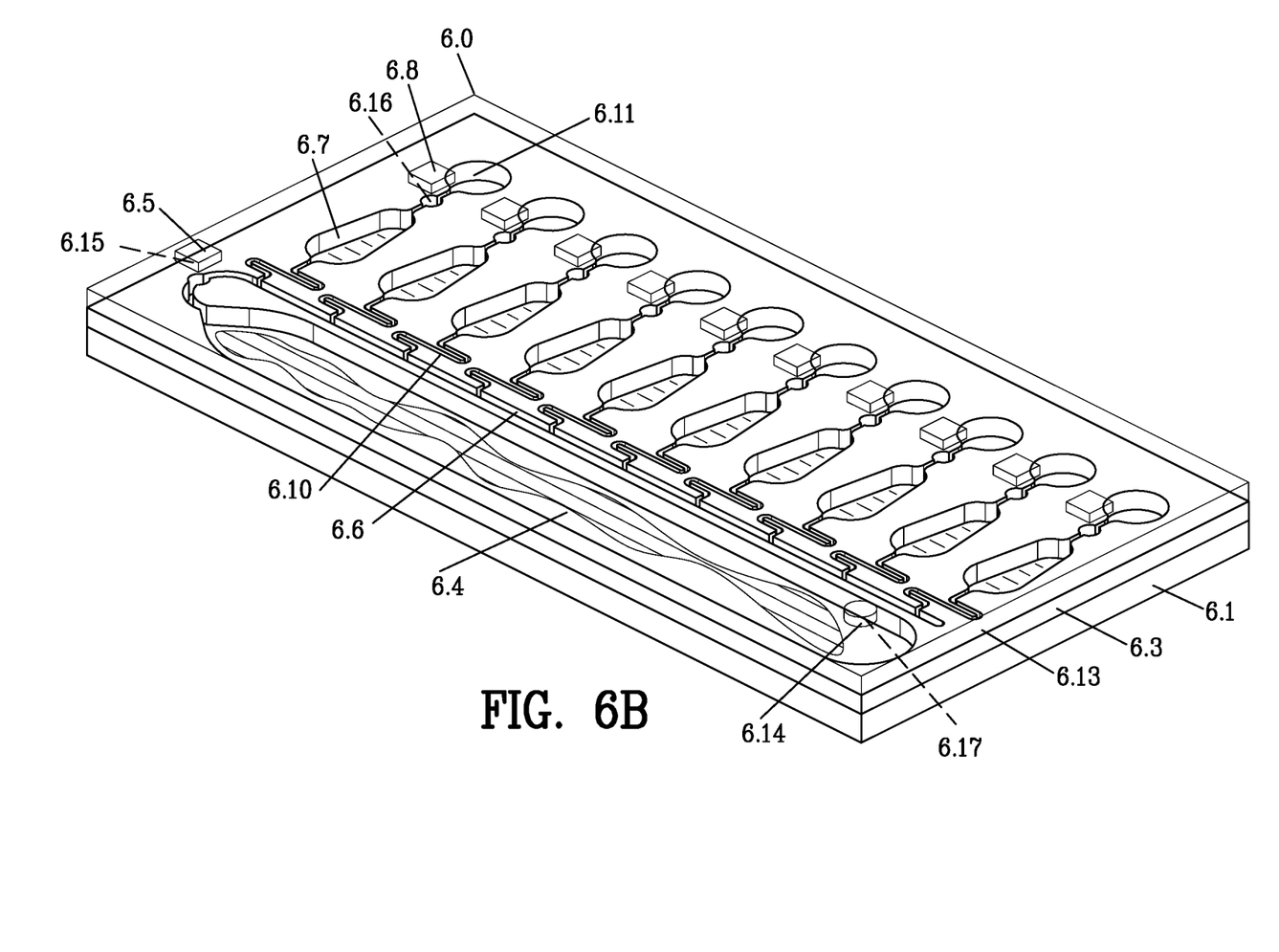
FIG. 6B illustrates the full assembly for the linear cartridge of FIG. 6A.

FIGS. 6A and 6B illustrates fourth embodiment of the invention incorporating the micro fluidic sampling device into a linear cartridge 6.0. In the prior embodiments shown in FIGS. 1-3 and 5, the main force to pump the liquid within the rotary disk was a centrifugal force. The main force to pump the liquid within the linear cartridge 6.0 is a vacuum and gravity.

Due to absence of centrifugal force, this device accepts the sample that already is centrifuged externally or just accepts the samples without it centrifuged. It means in the case of blood, all the cells will be present in the identification process. They might create some noises in the signals but their effect is minor. Even in the disk base device, samples can be moved to the reaction, chamber without getting centrifuged if disk doesn't rotate with high speed. The down side is the pathogen concentration will be low in the reaction chambers but system still works and produces the result.

FIGS. 6A and 6B illustrate the main reservoir 6.1 to bold the centrifuged or uncentrifuged sample. In this reservoir the sample is treated with focused laser beam to do cell lysing. A mechanical active micro-valve location 6.15 receives a main reservoir valve 6.5 to transfer liquid through a principal capillary micro channel 6.6 to distribute the sample into the collector reservoir 6.7. A micro siphon channel 610 stops the movement of the biomaterials horn collector reservoir 6.7 to the principle capillary channel 6.6. The specified enzymes are located in the collector reservoir 6.7 to de-cleave DNA and RNA. After process is done the collector reservoir valve 6.8 located in the aperture 6.16 will, be activated to pass the crRNA to the reaction chamber 6.11. Inside the reaction chamber protein CA 12/13, reporter RNA, gRNA are located as freeze dried. As soon as liquid enters to this region they start getting activated and if crRMA target nucleic acid and gRNA hybridized, then CAS 12/13 starts cleaving any reported RNA molecules.

Similar to the disk design of FIG. 5, each pathogen has its own exclusive collector reservoir 6.7 in this design. It is possible to connect all of the collector reservoirs 6.7 to each other and use only single valve to do the distribution to the reaction chamber 6.11.

Figure 7:
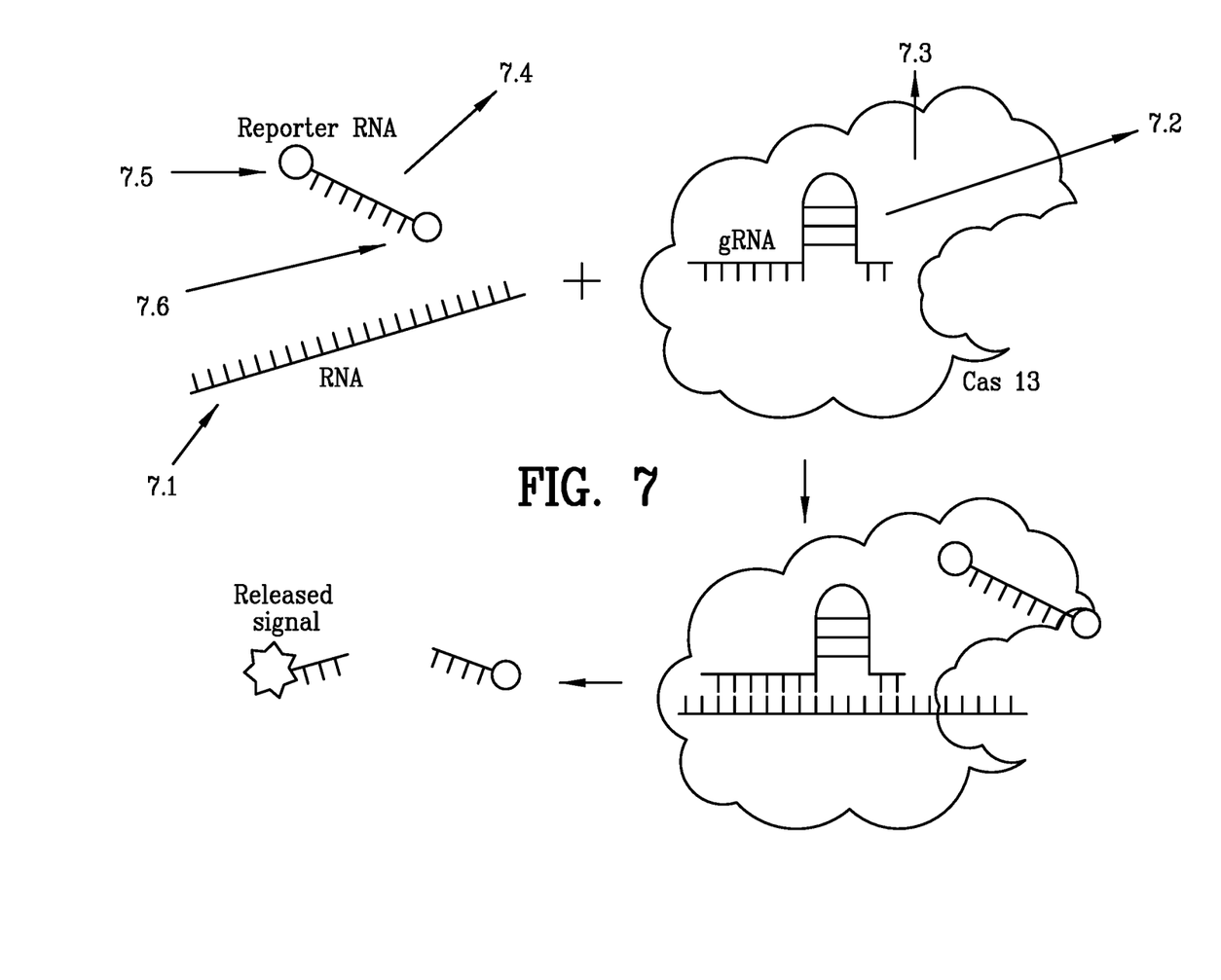
FIG. 7 is a schematic diagram of a reaction for the CAS 12/13 protein with gRNA.

FIG. 7 is presenting the presents the principle of CRISPER-CAS 13 diagnostics. Idea is to detect RNA 7.1. Biomaterials 7.2, 7.3 and 7.4 are loaded in the reaction chamber of the device disk. These materials are freeze dried and can be encapsulated inside a membrane. This membrane can be fabricated using biocompatible polyelectrolyte material that can form a complex with biomaterials and intact for a long time and get released in the presence of the liquid in the reaction chambers. This can hold the bio materials intact for a long time.

The gRNA 7.2 is designed similar to a key and is the key to detect the target genetic material 7.1 and consequently activate the CAS 13 protein 7.3. It is clear to the art that CAS 12 and CAS 13 are two different proteins that the first one activated by single strand and doable strand DNA segments, and second one by RNA molecules. CAS 12 unwinds the DNA by helicase activity, and hybridize it with the programmable gRNA, while CAS 13 however directly hybridizes fee target RNA molecule with gRNA without any needs to the unwinding process. Depending on the target genetic material type, both proteins can be used in the reaction chamber together or individually.

The 7.4 is presenting fluorescence labeled reporter RNA molecules. They are generally any RNA base combination of short oligonucleotide (20-30 base pairs) as shown as a bar in 7.4. Both ends connected to the quenching fluorescence molecules 7.5 and 7.6. 7.5 is designed to absorb blue light and fluoresce green light while the molecule 7.6 is designed to absorb green light and emit red light. If there is no hybridization in the reaction chamber means fee reporter RNA7.4 is not cut, when the reaction chamber is irradiated with blue light, the 7.5 molecule absorbs the blue light but since the molecule 7.6 is very close (less than 10 nm) to the green emitting fluorescence source it absorbs the green light and emits the red light. What observed is excitation by blue and emission of red light, no sign of green light. Now if the hybridization takes place between the target genetic material 7.1 and gRNA 7.2 then CAS 13 7.3 gets activated and reporter RNA7.4 gets an by CAS protein 7.3. This means the distance limitation between both fluorescence molecules of 7.5 and 7.6 are no longer exist and when the reaction chamber is illuminated with blue light, green light will be observed. Of course it might be still some unbroken reporter RNA feat emits red light. By applying filter for the red light clear green spectrum can be observed. This means that the pathogen in that specific chamber exists. Fluorescent emission can be detected either in real time or at the endpoint.

If the nucleic acid extraction takes place prior to the injection of the biological sample into the disk, or if the cell lysis is done through enzymatic or osmotic mechanism instead of using laser, then there won't be any needs for laser lying process. As a result, no extreme heat is generated then one can consider all the parts made with plastics molding. This can reduce the production costs since all the research is done with glass parts and final design can be made using plastic molding techniques.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A micro fluidic sampling device for rapid identification of a microorganism from a sample, the micro fluidic sampling device utilizing a grabber for engaging and rotating the micro fluidic sampling device, the micro fluidic sampling device utilizing a laser for producing a laser beam traversing the micro fluidic sampling device and entering a spectrometer detector, the micro fluidic sampling device containing a reactant, the micro fluidic sampling device, comprising:
   a rotary disk having a hole for enabling the grabber to hold and to rotate said rotary disk;
   a main reservoir in said rotary disk for receiving the sample;
   an inlet in said rotary disk for introducing the sample into said main reservoir;
   a capillary channel in said rotary disk and coupled to said main reservoir;
   a plurality of U-shaped micro channels in said rotary disk and coupled to said capillary channel;
   a main reservoir valve between said main reservoir and said capillary channel for controlling the flow of the sample from said main reservoir and into said plurality of U-shaped micro channels;
   a plurality of collection reservoirs in said rotary disk and coupled to each of said plurality of U-shaped micro channels;
   a plurality of reaction chambers in said rotary disk and coupled to said plurality of collection reservoirs;
   a plurality of collector reservoir valves between said plurality of collector reservoirs and said plurality of reaction chambers for preventing backflow of the sample from said plurality of reaction chambers into said plurality of collector reservoirs;
   said plurality of collection reservoirs containing the reactant for reacting with the sample; and
   said plurality of reaction chambers receiving the reactant and the sample for the laser beam from the laser to enter the spectrometer detector for rapid identification of the microorganism from the sample.

2. The micro fluidic sampling device as set forth in claim 1, wherein said rotary disk includes a base layer and a cover layer; and
   an inlet aperture in said cover layer for positioning the sample through said cover layer and into said main reservoir.

3. The micro fluidic sampling device as set forth in claim 1, wherein said rotary disk includes a base layer and a cover layer; and
   a main aperture in said cover layer for receiving said main reservoir valve.

4. The micro fluidic sampling device as set forth in claim 1, wherein said rotary disk includes a base layer acid a cover layer; and
   a collector aperture in said cover layer for receiving said collector reservoir valve.

5. The micro fluidic sampling device as set forth in claim 1, wherein said main reservoir valve and said collector reservoir valve includes a magneto-mechanical valve.

6. The micro fluidic sampling device as set forth in claim 1, wherein said main reservoir valve and said collector reservoir valve includes a liquid crystal elastomer valve.

* * * * *